US00PP27570P3

(12) United States Plant Patent
Ciccolella

(10) Patent No.: US PP27,570 P3
(45) Date of Patent: Jan. 17, 2017

(54) ***LIRIOPE MUSCARI* PLANT NAMED 'LIRSS'**

(50) Latin Name: *Liriope muscari*
Varietal Denomination: LIRSS

(71) Applicant: Vic Ciccolella, Oakville (AU)

(72) Inventor: Vic Ciccolella, Oakville (AU)

( * ) Notice: Subject to any disclaimer, the term of this patent is extended or adjusted under 35 U.S.C. 154(b) by 183 days.

(21) Appl. No.: 14/121,340

(22) Filed: Aug. 21, 2014

(65) Prior Publication Data

US 2016/0057918 P1 Feb. 25, 2016

(51) Int. Cl.
*A01H 5/12* (2006.01)

(52) U.S. Cl.
USPC ..... Plt./450

(58) Field of Classification Search
USPC ..... Plt./450
See application file for complete search history.

*Primary Examiner* — Keith Robinson
(74) *Attorney, Agent, or Firm* — Samuel R. McCoy, Jr.

(57) ABSTRACT

'LIRSS' is a distinctive variety of *Liriope muscari* which is characterized by a foliage variegation pattern with white-colored leaf striations that are significantly wider than the green-colored leaf striations, giving plants a general silver appearance.

1 Drawing Sheet

Latin name of the genus and species: The Latin name of the genus and species of the novel variety disclosed herein is *Liriope muscari*.

Variety denomination: The inventive variety of *Liriope muscari* disclosed herein has been given the variety denomination 'LIRSS'.

BACKGROUND OF THE INVENTION

The present invention relates to a new and distinct perennial variety of *Liriope muscari*, which has been given the variety denomination of 'LIRSS'. Its market class is that of an ornamental flowering perennial. 'LIRSS' is intended for use in landscaping and also in garden containers. *Liriope muscari*, commonly called "lilyturf", is an evergreen perennial native to China and Japan that forms clumps of dark green grass-like leaves with light lavender flower spikes that appear in summer. Its consistent size and performance through its hardiness range make it an ideal choice for specimen, borders and mass plantings in any filtered sun to shady, low maintenance landscape or container.

Parentage: In April 2007, a basal shoot with a higher degree of white striations was discovered growing from an unnamed variegated *Liriope muscari* stock plant (unpatented) at a wholesale nursery in Oakville, New South Wales, Australia. The instant mutation was isolated from the mother plant by way of dividing the plant's crown and said mutation was potted into a nursery container for further observation. The resulting plant was further grown and asexually propagated through five generations from April 2007 until January 2011, at which time it was determined that the characteristics for which the instant mutation was originally isolated were uniform and stable. The new plant was given the name 'LIRSS'

Asexual Reproduction: 'LIRSS' was first asexually propagated by dividing the root-bearing, rhizomatous propagules of the plant (i.e. "division cloning") in April of 2007 at a wholesale nursery in Oakville, New South Wales, Australia and has since been asexually propagated through five subsequent generations. The distinctive characteristics of the inventive 'LIRSS' variety are stable from generation to generation; clones of the variety produced by asexual reproduction maintain the distinguishing characteristics of the original plant.

SUMMARY OF THE INVENTION

'LIRSS' is a distinctive variety of *Liriope muscari* which is characterized by a parallel green and white foliage variegation pattern with white-colored leaf striations that are significantly wider than the green-colored leaf striations, giving plants a general silver appearance.

BRIEF DESCRIPTION OF THE FIGURES

The FIGURE shows an exemplary 'LIRSS' specimen, approximately 8 months of age, grown in 15 cm nursery pots.

BOTANICAL DESCRIPTION OF THE PLANT

The following is a detailed botanical description of a new and distinct variety of a *Liriope muscari* ornamental plant known as 'LIRSS'. Plant observations were made on plants grown in Awendaw, S.C. Unless indicated otherwise, the descriptions disclosed herein are based upon observations made in July 2013 of mature 'LIRSS' plants, approximately 8 months of age, grown from rooted cuttings planted in soilless potting media in 15 cm nursery pots. Plants were grown under cover of shade; fertilized with slow release granular fertilizer and regularly watered with overhead irrigation. No pest or disease measures were taken during production.

Those skilled in the art will appreciate that certain characteristics will vary with older or, conversely, younger plants. 'LIRSS' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on The Royal Horticultural Society Colour Chart, The Royal Horticultural Society, London, 1986 edition. Note that generic color descriptions such as 'green' do not exist in the RHS charts and the corresponding RHS colors are quoted.

Growth Habit, Dimensions and Color

Plant description:

*Plant habit*.—Rhizomatous herbaceous perennial with an arching habit and curled leaves.

*Height*.—20 cm, as measured.

*Width*.—35 cm, as measured.

*Bloom period*.—Summer.

*Hardiness*.—USDA Zone 6 to 10.

*Environmental tolerances*.—Prefers to be grown in partial shade although it is tolerant of full sun. Drought tolerant once established; moderate to good recovery with watering after severe wilting. Tolerates a wide range of soil types from sandy loam to loamy clay.

*Pest and disease susceptibility or resistance*.—No pests or diseases observed.

*Propagation*.—Propagation is accomplished through division of rhizomes.

*Time to initiate roots*.—Approximately 2.5 weeks

*Crop time*.—Depending on latitude of and microclimate of growing location, a fully rooted cutting requires approximately 3 months with an additional 5 to 7 months needed to produce a mature and marketable 15 cm container.

Roots: The roots of 'LIRSS' are fibrous and freely-branched, colored orange-white, RHS 159D, fleshy and thick with terminate tubers, similar to other *Liriope muscari*; high root density. Very short and tightly clumped subsurface rhizomes which root at nodes.

Stem:

*Branching habit*.—Acaulescent, rhizomatous plant with shoots emerging from rhizomes with an upright attitude.

Basal shoots:

*Shoots density*.—5 divisions, or propagules, per 15 cm nursery pot, with the oldest propagules near the center of the plant's crown possessing 34 leaves and shoots of varying ages and sizes.

*Shoot strength*.—Medium.

*Cross section*.—Convex.

*Shoot color* (*adaxial surfaces*).—Solid white corresponding to 157D.

*Shoot surface texture*.—Smooth.

Foliage:

*Type*.—Evergreen.

*Arrangement*.—Basal.

*Division*.—Simple.

*Attitude*.—Arched.

*Shape*.—Linear.

*Apex*.—Acute.

*Base*.—Sheathed.

*Sheath color*.—Greyed-orange 165B.

*Cross section*.—Convex.

*Venation*.—Parallel.

*Vein color* (*adaxial surfaces*).—Indistinguishable from the surrounding foliage.

*Vein color* (*abaxial surfaces*).—Indistinguishable from the surrounding foliage.

*Margins*.—Entire.

*Attachment*.—Acaulescent.

*Texture* (*adaxial and abaxial surfaces*).—Smooth and glossy.

*Surface hairiness* (*adaxial surface*).—Glabrous.

*Surfaces hairiness* (*abaxial surface*).—Glabrous.

*Mature leaf dimensions*.—Short and broad; length 320 mm, average width 7 mm at widest point.

*Mature leaf color* (*adaxial & abaxial surfaces*).—Variegated; comprised of thick parallel striations of white corresponding to 165D and fine parallel striations. Abaxial surface colors are the same, only with higher glaucosity giving the underside a slight sheen; i.e. silvered appearance.

*Petiole*.—Leaves are acaulescent; sessile.

*Stipules*.—Absent.

Inflorescence: The inflorescence is a raceme of approximately 8 to 10 cm long and 1.5 to 2.0 cm wide, consisting of approximately 80 to 120 pedicellate, simple flowers which are freely arranged in axillary fascicles of two to six. Each fascicle is subtended by a small lanceolate-shaped laminar bract, colored yellow-green 144B. Pedicels are strong, 3 to 4 mm long and approximately 1 mm wide. Pedicel color is red-purple 65B; pedicels are smooth and glabrous. Raceme length ranges from 7 to 9 cm. Peduncles are strong, and the length ranges from 10 to 14 cm with a diameter of 2 to 3 mm; raceme position is at or slightly above the foliage at anthesis. Peduncle color is yellow-green 144A and transitions to a combination of grey-purple 185C to 186D at the raceme; texture is smooth and glabrous.

Buds: Obovate flower buds are approximately 4 mm in length and 3 mm in width. Color is purple 78D.

Flowers: The flowering season is summer to autumn. Perianth is polypetalous with 6 tepals forming a cupped perianth, with a diameter ranging from 4 to 5 mm and a depth of 3.5 mm at anthesis. Mature tepal color on both the upper and lower surfaces is red-purple 65B, with a smooth texture. Margins entire. Apex is obtuse or rounded; base is rounded. Flowers are persistent and non-fragrant, each lasting 10 to 14 days.

Reproductive organs:

*Stamens*.—Stamen quantity — Six. Filament — Dimensions — Approximately 1.5 mm long. Color — Violet RHS 65D. Anther — Anther shape — Bilobate. Anther size — Less than 1 mm long. Anther color — Yellow RHS 5C. Pollen — None observed.

*Pistil*.—Pistil quantity — One club-shaped pistil. Pistil dimensions — 2.5 mm long and 1.5 mm wide. Stigma — Shape — Globose. Dimensions — Approximately 0.5 mm tall and 1.5 mm wide. Color — Violet RHS 65B. Style — Dimensions — 0.5 mm tall and 1.5 mm wide. Color — Violet RHS 65B. Ovary — Position — Superior. Dimensions — 1.0 mm tall and 1.5 mm wide. Color — Violet RHS 65D.

Fruit and seeds: Globose berries, approximately 5 mm in diameter, each containing one seed. Berries are glabrous, shiny and have a color that approximates to green 139A when immature and maturing to black 202A late in the season. Seeds are globose, approximately 3.5 mm wide and 3.5 mm long and black, 202A.

Comparison of 'LIRSS' with the Parent and Other Varieties of *Liriope muscari*

'LIRSS' is similar to the parent in most respects with the exception of the variegation pattern and, specifically, the thickness of the white-colored striations on the foliage. When compared with the parent, 'LIRSS' exhibits white-colored leaf striations that are significantly wider than the green-colored leaf striations. In 'LIRSS', white-colored striations range in thickness from less than 1 mm to 7 mm wide with the majority of these striations measuring between 2 to 5 mm wide. In contrast, the variegation pattern of the parent typically exhibits an equal number of green-colored and white-colored striations; both colors of striations typically being less than 1 mm wide. The wide white-colored leaf striations of 'LIRSS' give plants a general white or silvered appearance.

'LIRSS' is most similar to the commercial variety *Liriope muscari* 'Aztec Grass' (not patented). The leaf variegation patterns are similar, however the white striations of 'LIRSS' are thicker than those of 'Aztec Grass'. 'LIRSS' exhibits a high degree of plant vigor which translates to a faster growth rate compared to that of 'Aztec Grass'. 'LIRSS' is highly rhizomatous, whereas 'Aztec Grass' is moderately rhizomatous. The flowers of 'LIRSS' are red-purple, whereas the flowers of 'Aztec Grass' are light purple.

That which is claimed is:

1. A new and distinct variety of *Liriope muscari* plant named 'LIRSS', substantially as described and illustrated herein.

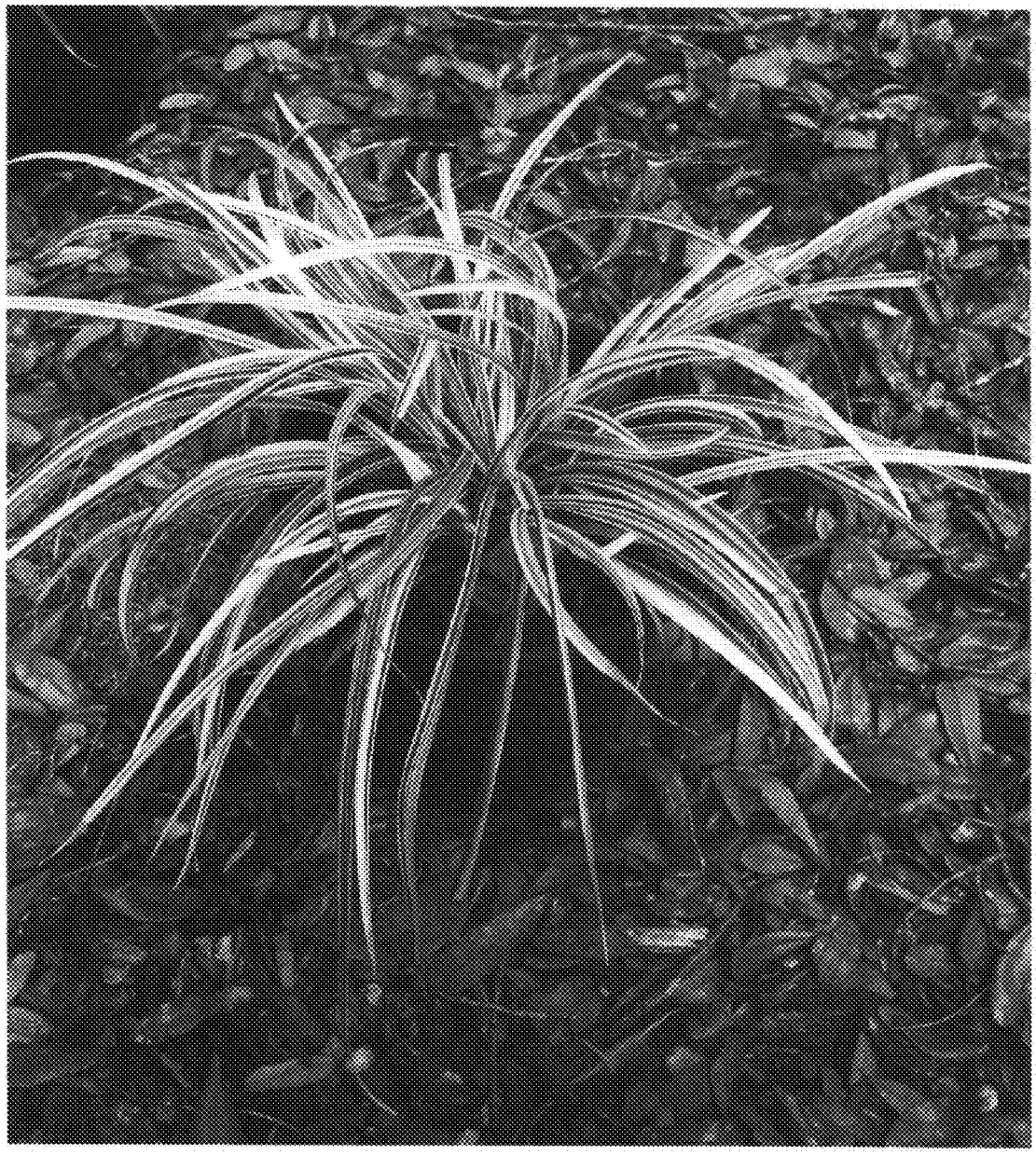

* * * * *